United States Patent
Bradley et al.

(10) Patent No.: US 7,619,107 B2
(45) Date of Patent: *Nov. 17, 2009

(54) COPPER (II) COMPLEXES FOR DEPOSITION OF COPPER FILMS BY ATOMIC LAYER DEPOSITION

(75) Inventors: Alexander Zak Bradley, Drexel Hill, PA (US); Jeffery Scott Thompson, Wilmington, DE (US); Kyung-Ho Park, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 284 days.

This patent is subject to a terminal disclaimer.

(21) Appl. No.: 11/658,369

(22) PCT Filed: Jul. 29, 2005

(86) PCT No.: PCT/US2005/026953

§ 371 (c)(1),
(2), (4) Date: Jan. 24, 2007

(87) PCT Pub. No.: WO2006/015200

PCT Pub. Date: Feb. 9, 2006

(65) Prior Publication Data

US 2008/0044687 A1  Feb. 21, 2008

(51) Int. Cl.
*C07F 1/08* (2006.01)
*B23B 9/04* (2006.01)
*C23C 16/00* (2006.01)
*C07C 211/22* (2006.01)

(52) U.S. Cl. .................. 556/110; 556/33; 564/509; 427/255.6; 428/704

(58) Field of Classification Search ............ 556/110, 556/33; 564/509
See application file for complete search history.

(56) References Cited

U.S. PATENT DOCUMENTS

| 4,130,652 A | 12/1978 | Ilvespaa et al. |
| 5,464,666 A | 11/1995 | Fine et al. |
| 6,464,779 B1 | 10/2002 | Powell et al. |
| 2003/0097013 A1 | 5/2003 | Chen et al. |
| 2003/0135061 A1 | 7/2003 | Norman et al. |

FOREIGN PATENT DOCUMENTS

| DE | 27 07 658 | 2/1977 |
| DE | 42 02 889 C2 | 8/1993 |
| WO | WO 00/09571 | 2/2000 |
| WO | WO 03/044242 A2 | 5/2003 |
| WO | WO 2004/036624 A2 | 4/2004 |
| WO | WO 2004/046417 A2 | 6/2004 |

OTHER PUBLICATIONS

Brown et al, "Experiments towards the synthesis of corrins. V.", Journal of the Chemical Society (1959), 2109-16.*
M. Ritala et al., Atomic Layer Deposition, Handbook of Thin Film Materials, 2001, vol. 1:103-159, Chapter 2.
S.G. McGeachin, Synthesis and Properties of Some B-Diketimines Derived From Acetylacetone, and Their Metal Complexes, Canadian Journal of Chemistry, 1968, vol. 46:1903-1912.
A. Eschenmoser, 70. Sulfidkontraktion Via Alkylative Kupplung: Eine Methode Zur Darstellung Von B-Dicarbonylderivaten, Helvetica Chemica Acta, 1971, vol. 54:710-734.
S. Fustero, New Strategies for the Synthesis of Fluorinated Vinylogous Amidines and B-Enamino Ketones, Journal of Organic Chemistry, 1999, vol. 64:5551-5556.

\* cited by examiner

*Primary Examiner*—Timothy H Meeks
*Assistant Examiner*—Joseph Miller, Jr.

(57) ABSTRACT

The present invention relates to novel 1,3-diimines and 1,3-diimine copper complexes and the use of 1,3-diimine copper complexes for the deposition of copper on substrates or in or on porous solids in an atomic layer deposition process.

1 Claim, No Drawings

COPPER (II) COMPLEXES FOR DEPOSITION OF COPPER FILMS BY ATOMIC LAYER DEPOSITION

FIELD OF THE INVENTION

The present invention relates to novel 1,3-diimines and 1,3-diimine copper complexes. The invention also relates to processes for forming copper deposits on substrates or in or on porous solids, using the 1,3-diimine copper complexes.

BACKGROUND

Atomic layer deposition (ALD) processes are useful for the creation of thin films, as described by M. Ritala and M. Leskela in "Atomic Layer Deposition" in *Handbook of Thin Film Materials*, H. S. Nalwa, Editor, Academic Press, San Diego, 2001, Volume 1, Chapter 2. Such films, especially metal and metal oxide films, are critical components in the manufacture of electronic circuits and devices.

In an ALD process for depositing copper films, a copper precursor and a reducing agent are alternatively introduced into a reaction chamber. After the copper precursor is introduced into the reaction chamber and allowed to adsorb onto a substrate, the excess (unadsorbed) precursor vapor is pumped or purged from the chamber. This process is followed by introduction of a reducing agent that reacts with the copper precursor on the substrate surface to form copper metal and a free form of the ligand. This cycle can be repeated if needed to achieve the desired film thickness.

This process differs from chemical vapor deposition (CVD) in the decomposition chemistry of the metal complex. In a CVD process, the complex undergoes pyrolytic decomposition on contact with the surface to give the desired film. In an ALD process, the complex is not completely decomposed to metal on contact with the surface. Rather, formation of the metal film takes place on introduction of a second reagent, which reacts with the deposited metal complex. In the preparation of a copper film from a copper(II) complex, the second reagent is a reducing agent. Advantages of an ALD process include the ability to control the film thickness and improved conformality of coverage because of the self-limiting adsorption of the precursor to the substrate surface in the first step of the process.

The ligands used in the ALD processes must also be stable with respect to decomposition and be able to desorb from the complex in a metal-free form. Following reduction of the copper, the ligand is liberated and must be removed from the surface to prevent its incorporation into the metal layer being formed.

U.S. Pat. No. 5,464,666 describes the decomposition of 1,3-diimine copper complexes in the presence of hydrogen to form copper. This patent also describes the use of 1,3-diimine copper complexes in a CVD process for producing copper-aluminum alloys.

DE 4202889 describes the use of 1,3-diimine metal complexes to deposit coatings, preferably via a CVD process. Decomposition of the metal complexes in a reducing atmosphere, preferably hydrogen, is disclosed.

S. G. McGeachin, *Canadian Journal of Chemistry*, 46, 1903-1912 (1968), describes the synthesis of 1,3-diimines and metal complexes of these ligands, including bis-chelate or homoleptic complexes of the form $ML_2$.

U.S. Pat. No. 6,464,779 discloses a Cu atomic layer CVD process that requires treatment of a copper precursor containing both oxygen and fluorine with an oxidizing agent to form copper oxide, followed by treatment of the surface with a reducing agent.

WO 2004/036624 describes a two-step ALD process for forming copper layers comprising forming a copper oxide layer from a non-fluorine containing copper precursor on a substrate and reducing the copper oxide layer to form a copper layer on the substrate. Copper alkoxides, copper β-diketonates and copper dialkylamides are preferred copper precursors. The reducing agent is a hydrogen ($H_2$) containing gas.

US 2003/0135061 discloses a dimeric copper(I) precursor that can be used to deposit metal or metal-containing films on a substrate under ALD or CVD conditions.

WO 2004/046417 describes the use of dimeric copper (i) complexes comprising amidinate ligands for use in an ALD process.

US 2003/097013 and WO03/044242 disclose an ALD process with a homoleptic copper(II) precursor with a symmetrical β-diketiminate ligand and reducing agent.

WO 09571 discloses an ALD process using a homoleptic copper(II) precursor with a symmetrical β-diketiminate ligand and reducing agent.

DE 2,707,658 and U.S. Pat. No. 4,130,652 describe the preparation of monocyclic β-ketimines having aromatic substituents.

A. Eschenmoser, Helvetica Chemica Acta, 1971, 54, No 70, 710, discloses sulfide contraction via alkylative coupling for the synthesis of secondary vinylogous amides and enolizable β-dicarbonyl compounds.

S. Fustero, Journal of Organic Chemistry, 1999, 64, 5551-5556, discloses strategies for the synthesis of fluorinated vinylogous amidines and β-enamino ketones.

SUMMARY OF THE INVENTION

One aspect of the present invention is a process for forming copper deposits on a substrate comprising:

a. contacting a substrate with a copper complex, (I), to form a deposit of a

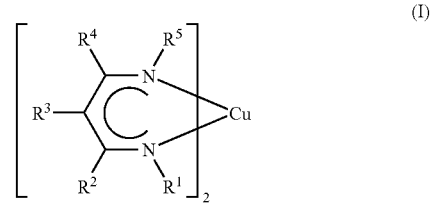

copper complex on the substrate; and b. contacting the deposited copper complex with a reducing agent, wherein $R^1$-$R^5$ are independently selected from hydrogen, methyl, ethyl, propyl, isopropyl, isobutyl, and neopentyl, with the proviso that at least one of ($R^1$, $R^2$) and ($R^4$, $R^5$) taken together is —$(CR^6R^7)_n$—, where $R^6$ and $R^7$ are independently selected from hydrogen, fluorine, trifluoromethyl, $C_1$-$C_5$ alkyl, and $C_1$-$C_5$ alkyl ester, and n is 3, 4 or 5; and the reducing agent is selected from 9-BBN (9-borabicyclo [3.3.1]nonane); diborane; boranes of the form $BR_xH_{3-x}$ where x=0, 1 or 2, and R is independently selected from phenyl and $C_1$-$C_{10}$ alkyl groups; dihydrobenzofuran; pyrazoline; disilane; silanes of the form $SiR'_yH_{4-y}$, where y=0, 1, 2 or 3, and R' is independently selected from phenyl and $C_1$-$C_{10}$ alkyl groups; and germanes of the form $GeR''_zH_{4-z}$, where $z=0, 1, 2$, or 3, and R" is independently selected from phenyl and $C_1$-$C_{10}$ alkyl groups.

Another aspect of this invention is a copper complex of structure (I).

Another aspect of this invention is a composition of structure (II)

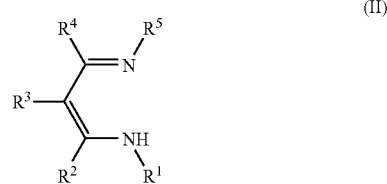

wherein $R^1$-$R^5$ are independently selected from methyl, ethyl, propyl, isopropyl, isobutyl, and neopentyl, with the proviso that each of ($R^1$, $R^2$) and ($R^4$, $R^5$) taken together is —$(CR^6R^7)_n$—, where $R^6$ and $R^7$ are independently selected from hydrogen, fluorine, trifluoromethyl, $C_1$-$C_5$ alkyl, and $C_1$-$C_5$ alkyl ester, and n is 3, 4 or 5.

DETAILED DESCRIPTION

Applicants have discovered an atomic layer deposition (ALD) process suitable for creation of copper films for use as seed layers in the formation of copper interconnects in integrated circuits, or for use in decorative or catalytic applications. This process uses copper (II) complexes that are volatile, thermally stable and derived from ligands that contain C, H, and N, but are not limited to these elements. The ligands are chosen to form copper (II) complexes that are volatile in an appropriate temperature range but do not decompose to copper metal in this temperature range. Rather, the complexes decompose to metal on addition of a suitable reducing agent. The ligands are further chosen so that they will desorb without decomposition upon exposure of the copper complex to a reducing agent. The reduction of these copper complexes to copper metal by readily available reducing agents has been demonstrated to proceed cleanly at moderate temperatures.

In a process of this invention, copper is deposited on a substrate by:

a. contacting a substrate with a copper complex, (I), to form a

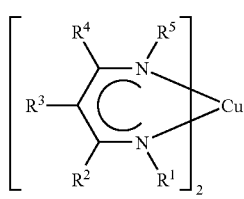

deposit of a copper complex on the substrate; and b. contacting the deposited copper complex with a reducing agent, wherein $R^1$-$R^5$ are independently selected from hydrogen, methyl, ethyl, propyl, isopropyl, isobutyl, and neopentyl, with the proviso that at least one of ($R^1$, $R^2$) and ($R^4$, $R^5$) taken together is —$(CR^6R^7)_n$—, where $R^6$ and $R^7$ are independently selected from hydrogen, fluorine, trifluoromethyl, $C_1$-$C_5$ alkyl, and $C_1$-$C_5$ alkyl ester, and n is 3, 4 or 5; and the reducing agent is selected from 9-BBN; diborane; boranes of the form $BR_xH_{3-x}$, where $x=0, 1$ or 2, and R is independently selected from phenyl and $C_1$-$C_{10}$ alkyl groups; dihydrobenzofuran; pyrazoline; disilane; silanes of the form $SiR'_yH_{4-y}$, where $y=0, 1, 2$ or 3, and R' is independently selected from phenyl and $C_1$-$C_{10}$ alkyl groups; and germanes of the form $GeR''_zH_{4-z}$, where $z=0, 1, 2$, or 3, and R" is independently selected from phenyl and $C_1$-$C_{10}$ alkyl groups.

The present deposition process improves upon conventional processes by allowing the use of lower temperatures and producing higher quality, more uniform films. The process of this invention also provides a more direct route to a copper film, avoiding the formation of an intermediate oxide film.

In a copper deposition process of this invention, the copper can be deposited on the surface, or in or on regions of porosity, of a substrate. Suitable substrates include conducting, semi-conducting and insulating substrates, including copper, silicon wafers, wafers used in the manufacture of ultra large scale integrated circuits, wafers prepared with dielectric material having a lower dielectric constant than silicon dioxide, and silicon dioxide and low k substrates coated with a barrier layer. Barrier layers to prevent the migration of copper include tantalum, tantalum nitride, titanium, titanium nitride, tantalum silicon nitride, titanium silicon nitride, tantalum carbon nitride, and niobium nitride.

The processes of the invention can be conducted in solution, i.e., by contacting a solution of the copper complex with the reducing agent. However, it is preferred to expose the substrate to a vapor of the copper complex, and then remove any excess copper complex (i.e., undeposited complex) by vacuum or purging before exposing the deposited complex to a vapor of the reducing agent. After reduction of the copper complex, the free form of the ligand can be removed via vacuum, purging, heating, rinsing with a suitable solvent, or a combination of such steps.

The process can be repeated to build up thicker layers of copper, or to eliminate pin-holes.

The deposition of the copper complex is typically conducted at 0 to 200° C. The reduction of the copper complex is typically carried out at similar temperatures, 0 to 200° C., more preferably 50 to 150° C.

In the processes of this invention, it is initially a copper complex that is deposited on the substrate. The formation of a metallic copper film does not occur until the copper complex is exposed to the reducing agent.

Aggressive reducing agents are used to reduce the copper complex rapidly and completely. Suitable reducing agents are volatile and do not decompose on heating. They are also of sufficient reducing power to react rapidly on contact with the copper complex deposited on the substrate surface. A group of suitable reducing agents has been identified that have been used for copper(II) reduction in an ALD process. One feature of suitable reducing reagents is the presence of a proton donor. The reducing agent is desirably able to transfer electrons to reduce the copper ion of the complex and protons to protonate the ligand. It is desirable that the oxidized reducing agent and the protonated ligand be easily removed from the surface of the newly formed copper deposit. Preferably, the protonated ligand is removed by vacuum, by purging or by flushing the surface with a suitable solvent.

Suitable reducing agents for the copper deposition processes of this invention include 9-BBN, borane, diborane, dihydrobenzofuran, pyrazoline, germanes, diethylsilane, dimethylsilane, ethylsilane, phenylsilane, silane and disilane. Diethylsilane and silane are preferred.

In one embodiment of a copper deposition process, the copper complexes are admitted to a reactor chamber containing the substrate under conditions of temperature, time and pressure to attain a suitable fluence of complex to the surface of the substrate. The selection of the variables temperature, time and pressure is determined by individual chamber and system design, and the desired process rate. After at least a portion of the copper complex has been deposited on the substrate, the undeposited complex vapor is pumped or purged from the chamber and the reducing agent is introduced into the chamber at a pressure of approximately 50 to 760 mTorr to reduce the adsorbed copper complex. The substrate is held at a temperature of approximately 0 to 200° C. during reduction. With suitable combinations of copper complex and reducing agent, this reduction is rapid and substantially complete. Desirably, the reaction is at least 95% complete within an exposure time of from less than a second to several minutes. It is desired that the products from this reaction are readily removed from the surface of the substrate.

In one embodiment of a process of this invention, the copper complex is a copper 1,3-diimine complex (I), wherein $R^1$ and $R^3$ are hydrogen groups, $R^2$ is a methyl group, $(R^4, R^5)$ taken together are —$(CR^6R^7)_n$—, where $R^6$ and $R^7$ are independently selected from hydrogen, fluorine, trifluoromethyl, $C_1$-$C_5$ alkyl, and $C_1$-$C_5$ alkyl ester, n is 3, and the reducing agent is diethylsilane. In one embodiment, $R^6$ and $R^7$ are H.

This invention also provides novel 1,3-diimine copper complexes,

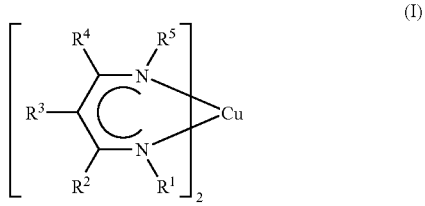

(I), where $R^1$-$R^5$ are independently selected from hydrogen, methyl, ethyl, propyl, isopropyl, isobutyl, and neopentyl, with the proviso that at least one of $(R^1, R^2)$ and $(R^4, R^5)$ taken together is —$(CR^6R^7)_n$—, where $R^5$ and $R^7$ are independently selected from hydrogen, fluorine, trifluoromethyl, $C_1$-$C_5$ alkyl, and $C_1$-$C_5$ alkyl ester, and n is 3, 4 or 5.

The synthesis of one ligand useful for making the copper complexes of this invention is given in Example 1, below. Other ligands can be prepared similarly. Thus, a cyclic ketimine can be deprotonated by strong base, and then treated with an electrophile such as ester or acid halide derivative to provide a keto cyclic enamine as an intermediate. Treatment of this intermediate with an alkylating agent such as dimethylsulfate, followed by the addition of a primary amine affords the desired cyclic diketimine. Alternatively, the cyclic ketimine, after deprotonation by strong base, can be directly coupled with an imidoyl derivative to provide the desired cyclic diketimine.

In another embodiment, this invention provides an article comprising a 1,3-diimine copper complex of structure (I)

deposited on a substrate. Suitable substrates include: copper, silicon wafers, wafers used in the manufacture of ultra large scale integrated circuits, wafers prepared with dielectric material having a lower dielectric constant than silicon dioxide, and silicon dioxide and low k substrates coated with a barrier layer. Barrier layers can be used to prevent the migration of copper into the substrate. Suitable barrier layers include: tantalum, tantalum nitride, titanium, titanium nitride, tantalum silicon nitride, titanium silicon nitride, tantalum carbon nitride, and niobium nitride.

One embodiment of this invention is a composition of structure (II),

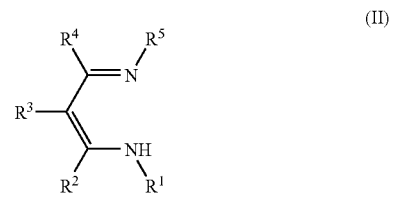

wherein $R^1$-$R^5$ are independently selected from methyl, ethyl, propyl, isopropyl, isobutyl, and neopentyl, with the proviso that each of $(R^1, R^2)$ and $(R^4, R^5)$ taken together is —$(CR^6R^7)_n$—, where $R^6$ and $R^7$ are independently selected from hydrogen, fluorine, trifluoromethyl, $C_1$-$C_5$ alkyl, and $C_1$-$C_5$ alkyl ester, and n is 3, 4 or 5.

EXAMPLES

Unless otherwise stated, all organic reagents are available from Sigma-Aldrich Corporation (Milwaukee, Wis., USA). $^1$H NMR data are reported in ppm relative to deuterated methylenechloride (5.32 ppm). $^{13}$C NMR data are reported in ppm relative to deuterated methylenechloride (53.8 ppm).

Example 1

Preparation of [2-(4,5-Dihydro-3H-pyrrol-2-yl)-1-methyl-vinyl]-ethyl-amine

To a solution of diisopropylamine (22.2 g, 219.3 mmol) in THF (200 mL) was dropwise added n-BuLi (2.89 M, 75.9 mL, 219.3 mmol) at −78° C. under nitrogen. Once all the n-BuLi was added, the temperature was adjusted to −5° C., and the reaction mixture was stirred for 30 min. Then a solution of 2-methyl-1-pyrroline (11.3 g, 135.7 mmol) in THF (15 mL) was added dropwise to the reaction mixture at −5° C., and then stirred. After 30 min, ethylacetate (9.20 g, 104.4 mmol) was added dropwise over 30 min. The reaction mixture was stirred as the temperature was allowed to gradually rise to room temperature, and was continuously stirred at room temperature overnight. THF solvent was removed under reduced pressure, then 80 mL of methanol was added dropwise to the residue. After removing all of the volatile solvent, diethyl ether (100 mL) was added to the residue, and the mixture was filtered. Concentration of the filtrate under reduced pressure, followed by column chromatography, provided the desired product.

The isolated material (5 g, 39.94 mmol) was treated with dimethlysulfate (5.04 g, 39.94 mmol) by stirring at room temperature overnight. THF (50 mL) was added to the resultant mixture, followed by the addition of an ethylamine solution (25.9 mL, 2.0 M in THF). After overnight reaction at room temperature, the solvent was removed under reduced pressure, followed by addition of sodium methoxide (39.94 mmol) solution (2.16 g of MeONa in 10 mL of MeOH). After stirring the mixture at room temperature for 30 min, the reaction mixture was concentrated under reduced pressure. Pentane (100 mL) was added to the residue, then the insoluble material was filtered. Concentration of the filtrate under reduced pressure afforded almost pure diketimine product (5.6 g), which was purified by vacuum distillation (37° C. at 50 mTorr) to afford 5.47 g (90% yield) of liquid.

Example 2

Preparation of 2-(Pyrrolidin-2-ylidenemethyl)-1-pyrroline

To a solution of diisopropylamine (11.1 g, 109.7 mmol) in THF (200 mL) was dropwise added n-BuLi (2.89 M, 37.97 mL, 109.7 mmol) at −78° C. under nitrogen. Once all the n-BuLi was added, the temperature was adjusted to −5° C., and the reaction mixture was stirred for 30 min. Then a solution of 2-methyl-1-pyrroline (5.65 g, 67.9 mmol) in THF (15 mL) was added dropwise to the reaction mixture at −5° C., and then stirred. After 30 min, 2-methylthio-1-pyrroline (6.02 g, 52.3 mmol) was added dropwise over 30 min at −78° C. The reaction mixture was stirred as the temperature was allowed to gradually rise to room temperature, and was continuously stirred at room temperature overnight. THF solvent was removed under reduced pressure, then 50 mL of methanol was added dropwise to the residue. After removing all of the volatile solvent, pentane (2×100 mL) was added to the residue, and the mixture was filtered. Concentration of the filtrate under reduced pressure, followed by vacuum distillation (65° C. at 110 mTorr), delivered 6.29 of product (79%). $^1$H NMR (CD$_2$Cl$_2$, 500 MHz): δ 7.89 (s, br, 1H), 4.65 (s, 1H), 3.64 (t, 2H, J=7.2 Hz), 2.51 (t, 2H, J=8.0 Hz), 1.85 (m, 2H). $^{13}$C NMR (CD$_2$Cl$_2$, 125 MHz): δ 167.0, 81.7, 53.7, 34.8, 23.2.

Example 3

Preparation of 2-(1-Pyrrolin-2-ylmethylene)piperidine

To a solution of diisopropylamine (6.32 g, 62.52 mmol) in THF (100 mL) was dropwise added n-BuLi (2.89 M, 21.63 mL, 62.52 mmol) at −78° C. under nitrogen. Once all the n-BuLi was added, the temperature was adjusted to −5° C., and the reaction mixture was stirred for 30 min. Then a solution of 2-methyl-3,4,5,6-tetrahydropyridine (3.76 g, 38.70 mmol) in THF (15 mL) was added dropwise to the reaction mixture at −5° C., and then stirred. After 30 min, 2-methylthio-1-pyrroline (3.43 g, 29.77 mmol) was added dropwise over 30 min at −78° C. The reaction mixture was stirred as the temperature was allowed to gradually rise to room temperature, and was continuously stirred at room temperature overnight. THF solvent was removed under reduced pressure, then 30 mL of methanol was added dropwise to the residue. After removing all of the volatile solvent, pentane (2×50 mL) was added to the residue, and the mixture was filtered. Concentration of the filtrate under reduced pressure, followed by vacuum distillation (75° C. at 185 mTorr) delivered 4.1 g of product (84%). $^1$H NMR (CD$_2$Cl$_2$, 500 MHz): δ 9.64 (s, br, 1H), 4.48 (s, 1H), 3.78 (t, 2H, J=7.3 Hz), 3.27 (t, 2H, J=6.1 Hz), 2.45 (m, 2H), 2.33 (t, 2H, J=6.2 Hz), 1.73 (m, 4H), 1.67 (m, 2H). $^{13}$C NMR (CD$_2$Cl$_2$, 125 MHz): δ 173.6, 155.8, 86.5, 60.0, 41.7, 37.9, 29.5, 23.8, 22.7, 21.3.

Example 4

Preparation and Reduction of Bis[[2-(4,5-Dihydro-3H-pyrrol-2-yl)-1-methyl-vinyl]-ethyl-aminate]copper(II)

In a dry box, Cu(OEt)$_2$ (0.504 g, 3.28 mmol) and a 1,3-diketimine, {[2-(4,5-dihydro-3H-pyrrol-2-yl)-1-methyl-vinyl]-ethyl-amine, 1 g, 6.56 mmol} were mixed together in toluene (30 mL), and the resultant solution was stirred at room temperature overnight. The solution was filtered, and the filtrate was concentrated under reduced pressure. The resultant solid was recrystallized in pentane to afford a purple solid (1.1 g, 92% yield). This material was sublimed at 30° C. under 50 mTorr, and reduced to copper metal at 100° C. by diethylsilane as a reducing agent.

What is claimed is:
1. A 1,3-diimine copper complex, (I),

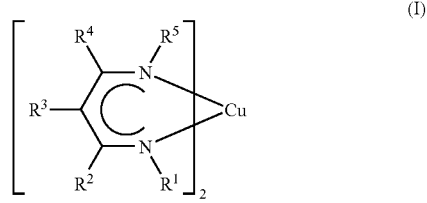

wherein
R$^1$ and R$^3$ are hydrogen and R$^2$ is methyl,
and (R$^4$, R$^5$) taken together are —(CR$^6$R$^7$)$_n$—, where R$^6$ and R$^7$ are independently selected from hydrogen, fluorine, trifluoromethyl, C$_1$-C$_5$ alkyl, and C$_1$-C$_5$ alkyl ester, and n is 3.

* * * * *